US00PP20206P2

(12) United States Plant Patent
Kako et al.

(10) Patent No.: US PP20,206 P2
(45) Date of Patent: Aug. 4, 2009

(54) ***TORENIA* PLANT NAMED 'SUNRENIBEBU'**

(50) Latin Name: ***Torenia* sp.**
Varietal Denomination: Sunrenibebu

(75) Inventors: Tetsuya Kako, Shiga (JP); Kiyoshi Miyazaki, Shiga (JP); Kazunari Iwaki, Kanagawa (JP); Takeshi Kanaya, Shiga (JP); Kenichi Suzuki, Osaka (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/157,321

(22) Filed: Jun. 9, 2008

(51) Int. Cl.
*A01H 5/00* (2006.01)

(52) U.S. Cl. ..... Plt./487

(58) Field of Classification Search ..... Plt./487
See application file for complete search history.

*Primary Examiner*—Annette H Para
(74) *Attorney, Agent, or Firm*—C. A. Whealy

(57) ABSTRACT

A new and distinct cultivar of *Torenia* plant named 'Sunrenibebu' characterized by its compact and mounding to trailing plant habit; freely branching habit; freely flowering habit; long flowering period; light violet-colored flowers; and good garden performance.

1 Drawing Sheet

Botanical designation: *Torenia* sp.
Cultivar denomination: 'Sunrenibebu'.

BACKGROUND OF THE INVENTION

The present invention relates to a new and distinct cultivar of *Torenia,* botanically known as *Torenia* sp. and hereinafter referred to by the name 'Sunrenibebu'.

The new *Torenia* is a whole plant mutation of a proprietary selection of *Torenia sp.* identified as code number TH4, not patented. The new *Torenia* was discovered and selected by the Inventors as a single plant in a controlled greenhouse environment in Higashiomi, Shiga, Japan in March, 2006.

Asexual reproduction of the new Torenia by vegetative cuttings in a controlled greenhouse environment in Higashiomi, Shiga, Japan since October, 2006, has shown that the unique features of this new *Torenia* are stable and reproduced true to type in successive generations.

SUMMARY OF THE INVENTION

Plants of the new *Torenia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunrenibebu'. These characteristics in combination distinguish 'Sunrenibebu' as a new and distinct cultivar of *Torenia:*

1. Compact and mounding to trailing plant habit.
2. Freely branching habit.
3. Freely flowering habit.
4. Long flowering period.
5. Light violet-colored flowers.
6. Good garden performance.

Plants of the new *Torenia* differ primarily from plants of the parent selection in flower color as plants of the parent selection have darker violet-colored flowers. In addition, plants of the new *Torenia* are smaller than plants of the parent selection.

Plants of the new *Torenia* can also be compared to plants of *Torenia* sp. 'Sunrenicopalave', disclosed in U.S. Plant Pat. No. 17,001. In side-by-side comparisons conducted in Higashiomi, Shiga, Japan, plants of the new *Torenia* and 'Sunrenicopalave' differed in the following characteristics:

1. Plants of the new *Torenia* were narrower than plants of 'Sunrenicopalave'.
2. Plants of the new *Torenia* had shorter internodes than plants of 'Sunrenicopalave'.
3. Plants of the new *Torenia* had narrower leaves than plants of 'Sunrenicopalave'.
4. Plants of the new *Torenia* had smaller flowers than plants of 'Sunrenicopalave'.
5. Plants of the new *Torenia* and 'Sunrenicopalave' differed in flower color as plants of 'Sunrenicopalave' had darker-colored flowers.
6. Plants of the new *Torenia* had shorter peduncles than plants of 'Sunrenicopalave'.

BRIEF DESCRIPTION OF THE PHOTOGRAPHS

The accompanying colored photographs illustrate the overall appearance of the new *'Torenia,* showing the colors as true as it is reasonably possible to obtain in colored reproductions of this type. Colors in the photographs may differ slightly from the color values cited in the detailed botanical description which accurately describe the colors of the new *Torenia.*

The photograph at the top of the sheet comprises a side perspective view of a typical flowering plant of 'Sunrenibebu' grown in a container.

The photograph at the bottom of the sheet is a close-up view of a typical flower, flower buds and leaves of 'Sunrenibebu'.

DETAILED BOTANICAL DESCRIPTION

The aforementioned photographs and following observations, measurements and values describe plants grown in Higashiomi, Shiga, Japan, under commercial practice during the autumn in a polyethylene-covered greenhouse with day temperatures averaging 20° C. and night temperatures averaging 10° C. Plants had been growing for five months when the photographs and description were taken. In the following description, color references are made to The Royal Horticultural Society Colour Chart, 2001 Edition, except where general terms of ordinary dictionary significance are used.

Botanical classification: *Torenia* sp. 'Sunrenibebu'.

Parentage: Whole plant mutation of a proprietary selection of *Torenia* sp. identified as code number TH4, not patented.

Propagation:

*Type.*—By vegetative cuttings.

*Time to initiate roots.*—About one week at 20° C. to 25° C.

*Time to produce a rooted young plant roots.*—About three to four weeks at 20° C. to 25° C.

*Root description.*—Fine, fibrous and fleshy; brown in color.

*Rooting habit.*—Freely branching.

Plant description:

*Plant form/habit.*—Compact and mounded to trailing plant habit; outwardly spreading; vigorous growth habit. Freely branching habit; pinching enhances branching; about 30 lateral branches develop per plant.

*Plant height.*—About 16.5 cm.

*Plant width (spread).*—About 45.4 cm.

*Lateral branches.*—Length: About 25.5 cm. Diameter: About 1.6 mm. Internode length: About 2.8 cm. Aspect: Decumbent. Texture: Smooth, glabrous. Color: Close to N144A.

Foliage description:

*Arrangement.*—Opposite, simple.

*Length.*—About 2.2 cm.

*Width.*—About 1.6 cm.

*Shape.*—Ovate.

*Apex.*—Acute.

*Base.*—Cordate.

*Margin.*—Serrate.

*Texture, upper surface.*—Pubescent.

*Texture, lower surface.*—Smooth, glabrous.

*Venation pattern.*—Pinnate; reticulate.

*Color.*—Developing and fully expanded leaves, upper surface: Close to 144A; venation, close to 145B. Developing and fully expanded leaves, lower surface: Close to 144B; venation, close to 145B.

*Petiole.*—Length: About 5 mm. Diameter: About 0.8 mm. Texture, upper and lower surfaces: Smooth, glabrous. Color, upper and lower surfaces: Close to 145B.

Flower description:

*Flower type/habit.*—Single flowers borne in upper leaf axils; corolla bilabiate and calyx tubular; flowers face obliquely upright. Freely flowering habit with about 64 open flowers per plant.

*Fragrance.*—None detected.

*Natural flowering season.*—Long flowering period; continuously flowering from early summer to late autumn in Japan. Flowers not persistent.

*Postproduction longevity.*—Flowers last about four days on the plant.

*Flower buds.*—Height: About 1.4 cm. Diameter: About 5 mm. Shape: Lenticular. Color: Close to N82B.

*Flower diameter.*—About 3 cm by 2.5 cm.

*Flower depth.*—About 3.4 cm.

*Throat diameter.*—About 9.3 mm.

*Tube diameter, base.*—About 3.2 mm.

*Tube length.*—About 2.3 cm.

*Petals.*—Quantity per flower: One upper or banner petal, two lateral petals and one lower petal in a single whorl, fused. Upper petal: Length: About 1 cm. Width: About 1.7 cm. Shape: Elliptic. Apex: Mucronate to truncate. Margin: Entire; slightly undulating. Texture, upper and lower surfaces: Smooth, glabrous; velvety. Color: Developing petals, upper surface: Close to 82C; towards the throat, close to 91D. Developing petals, lower surface: Close to 82C. Fully developed petals, upper surface: Close to 85C; towards the throat, close to 91D. Fully developed petals, lower surface: Close to 85C. Lateral petals: Length: About 9 mm. Width: About 1.4 cm. Shape: Elliptic. Apex: Truncate. Margin: Entire. Texture, upper and lower surfaces: Smooth, glabrous; velvety. Color: Developing petals, upper and lower surfaces: Close to 82C. Fully developed petals, upper and lower surfaces: Close to 85C. Lower petal: Length: About 1 cm. Width: About 1.4 cm. Shape: Elliptic. Apex: Rounded. Margin: Entire. Texture, upper and lower surfaces: Smooth, glabrous; velvety. Color: Developing petals, upper surface: Close to 82C; towards the throat, close to 91D. Developing petals, lower surface: Close to 82C. Fully developed petals, upper surface: Close to 85C; towards the throat, close to 91D. Fully developed petals, lower surface: Close to 85C. Throat color: Close to N82C; lines, close to N79B. Tube color: Close to N82A to N82B.

*Sepals.*—Quantity per flower: Typically five fused into two lobes; margins winged. Calyx length: About 1.6 cm. Calyx diameter: About 7.8 mm. Texture, upper and lower surfaces: Smooth, glabrous. Color, upper and lower surfaces: Close to 145D; wings, close to 144B.

*Peduncles.*—Length: About 1.7 cm. Diameter: About 1.1 mm. Texture: Smooth, glabrous. Color: Close to 144B.

*Reproductive organs.*—Stamens: Quantity per flower: Typically four; two pairs of fused anthers. Filament length: About 3.1 mm to 12.4 mm. Anther shape: Ellipsoidal. Anther size: About 3.3 mm by 0.7 mm. Anther color: Close to 155C. Pollen amount: Scarce. Pollen color: Close to 11B. Pistils: Quantity per flower: One. Pistil length: About 2.5 cm. Stigma shape: Elliptic. Stigma color: Close to 76D. Style color: Close to 77D. Ovary color: Close to 144A.

*Seed/fruit.*—Seed and fruit development have not been observed on plants of the new *Torenia*.

Disease/pest resistance: Plants of the new *Torenia* have not been noted to be resistant to pathogens and pests common to *Torenia*.

Garden performance: Plants of the new *Torenia* have been observed to have good garden performance and to tolerate rain, wind and temperatures from about 5° C. to about 30° C.

It is claimed:

1. A new and distinct *Torenia* plant named 'Sunrenibebu' as illustrated and described.

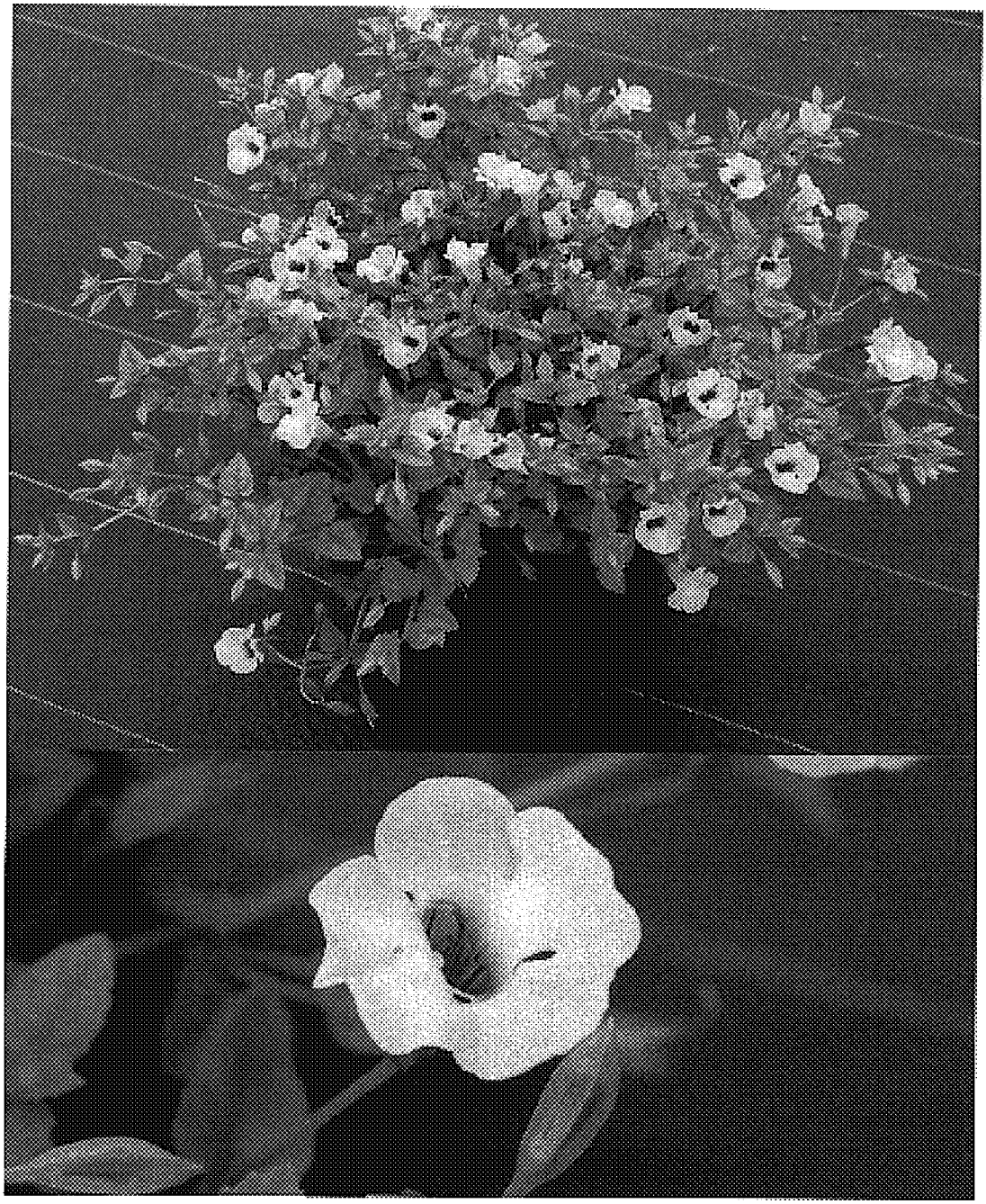

* * * * *